US012509678B2

(12) United States Patent
Ikeda et al.

(10) Patent No.: US 12,509,678 B2
(45) Date of Patent: Dec. 30, 2025

(54) MAGNETIC BEAD REAGENT

(71) Applicant: SEIKO EPSON CORPORATION, Tokyo (JP)

(72) Inventors: Yasunari Ikeda, Shiojiri (JP); Michio Nakamori, Matsumoto (JP); Hirofumi Hokari, Chino (JP); Masato Hanamura, Shiojiri (JP)

(73) Assignee: SEIKO EPSON CORPORATION (JP)

( * ) Notice: Subject to any disclaimer, the term of this patent is extended or adjusted under 35 U.S.C. 154(b) by 671 days.

(21) Appl. No.: 17/948,411

(22) Filed: Sep. 20, 2022

(65) Prior Publication Data

US 2023/0087918 A1 Mar. 23, 2023

(30) Foreign Application Priority Data

Sep. 21, 2021 (JP) ................................ 2021-153106

(51) Int. Cl.

| | |
|---|---|
| ***H01F 1/24*** | (2006.01) |
| ***C12N 15/10*** | (2006.01) |
| ***H01F 1/00*** | (2006.01) |
| ***H01F 1/153*** | (2006.01) |
| ***H01F 1/28*** | (2006.01) |

(52) U.S. Cl.
CPC ..... *C12N 15/1013* (2013.01); *H01F 1/15308* (2013.01)

(58) Field of Classification Search
CPC .......... H01F 1/53; H01F 1/20; H01F 1/15366; H01F 1/15383; H01F 1/24; H01F 1/28; H01F 1/0054; C12N 15/15308
See application file for complete search history.

(56) References Cited

U.S. PATENT DOCUMENTS

2007/0116600 A1* 5/2007 Kochar ................ B01L 3/5082 422/65

FOREIGN PATENT DOCUMENTS

| | | | | |
|---|---|---|---|---|
| JP | 2009-033995 A | | 2/2009 | |
| JP | 2011-234671 A | | 11/2011 | |
| JP | 2014-030364 A | | 2/2014 | |
| WO | WO-2021055083 A1 | * | 3/2021 | ......... C12N 15/1013 |

* cited by examiner

*Primary Examiner* — Matthew E. Hoban
*Assistant Examiner* — Lynne Edmondson
(74) *Attorney, Agent, or Firm* — Harness, Dickey & Pierce, P.L.C.

(57) ABSTRACT

A magnetic bead reagent contains: a magnetic bead containing a Fe-based metal soft magnetic particle and a silica film that has an average thickness of 20 nm or more and that covers the Fe-based metal soft magnetic particle; a surfactant; and a dispersion medium in which the magnetic bead is dispersed. The surfactant may be a nonionic surfactant.

5 Claims, 1 Drawing Sheet

MAGNETIC BEAD REAGENT

The present application is based on, and claims priority from JP Application Serial Number 2021-153106, filed Sep. 21, 2021, the disclosure of which is hereby incorporated by reference herein in its entirety.

BACKGROUND

1. Technical Field

The present disclosure relates to a magnetic bead reagent.

2. Related Art

A magnetic bead separation method is known as a method for extracting a target molecule such as a protein, an antibody, a peptide, or a nucleic acid. Since the magnetic bead separation method is a bead separation and recovering method by using magnetic force, a quick separation operation can be performed.

For example, JP-A-2009-33995 discloses that a nucleic acid is extracted from a blood sample by using highly magnetized magnetic beads each including an Fe metal core and a silica coating film, and a dissolution and binding liquid, the nucleic acid is separated and collected by using a combination of a permanent magnet and adsorption of a target biological material on surfaces of the beads, and nucleic acid extraction can be automated.

JP-A-2009-33995 further discloses that the highly magnetized magnetic beads are dispersed in advance in a buffer solution or a polar organic solvent. In addition, it is disclosed that a recovery amount of the nucleic acid is increased by performing such an operation.

In the nucleic acid extraction method described in JP-A-2009-33995, aggregation may occur when the highly magnetized magnetic beads are dispersed in advance. When the aggregation of the highly magnetized magnetic beads occurs, redispersibility decreases, which leads to a reduction in efficiency of cleaning the highly magnetized magnetic beads on which the nucleic acid is adsorbed or eluting the nucleic acid.

In addition, when the aggregation of the highly magnetized magnetic beads occurs, the silica coating films are damaged by friction between the highly magnetized magnetic beads when the highly magnetized magnetic beads are subjected to stirring by an ultrasonic treatment. When the silica coating films are damaged, the cores are exposed, so that Fe ions are eluted. The eluted Fe ions cause a decrease in recovery amount of the nucleic acid.

SUMMARY

A magnetic bead reagent according to an application example of the present disclosure contains: a magnetic bead containing a Fe-based metal soft magnetic particle and a silica film that has an average thickness of 20 nm or more and that covers the Fe-based metal soft magnetic particle; a surfactant; and a dispersion medium in which the magnetic bead is dispersed.

DESCRIPTION OF EXEMPLARY EMBODIMENTS

Hereinafter, a preferred embodiment of a magnetic bead reagent according to the present disclosure will be described in detail with reference to the accompanying drawings.

1. Method for Extracting Target Molecule

First, an example of a method for extracting a target molecule using a magnetic bead reagent will be described. Examples of the target molecule include a protein, an antibody, a peptide, and a nucleic acid. In the following description, a case in which the target molecule is a nucleic acid will be described, but the same applies to other target molecules. The nucleic acid may be present in a state of being contained in, for example, a biological sample such as a cell or biological tissue, a virus, or a bacterium. In addition, the nucleic acid may be a deoxyribonucleic acid (DNA) or a ribonucleic acid (RNA).

Figure 1:
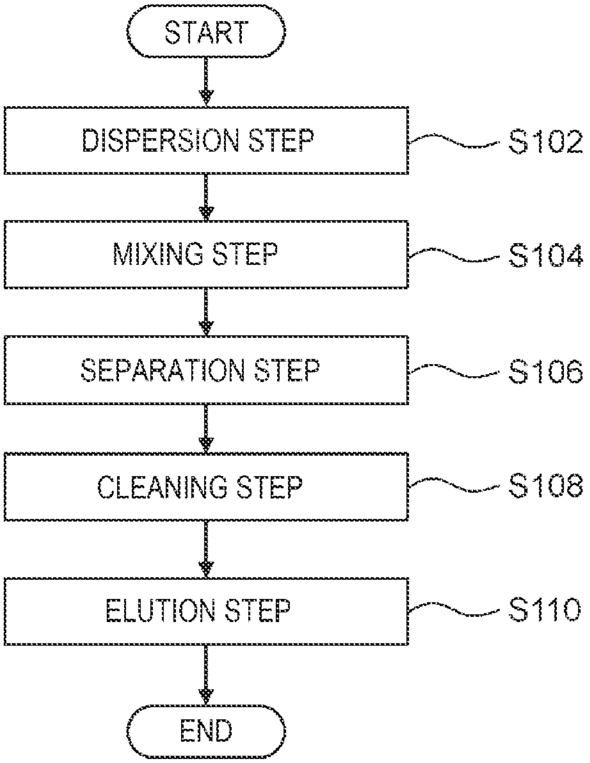
FIG. 1 is a flowchart showing an example of a nucleic acid extraction method using a magnetic bead reagent.
Figure 2:
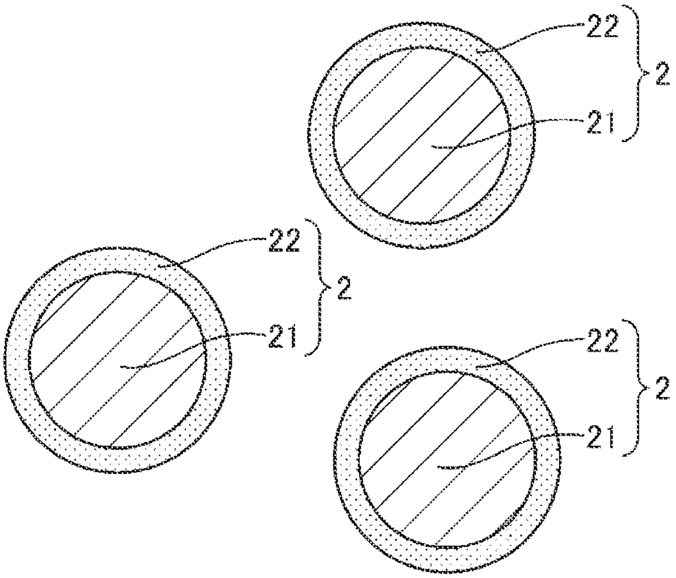
FIG. 2 is a cross-sectional view schematically showing magnetic beads contained in the magnetic bead reagent according to an embodiment.

FIG. 1 is a flowchart showing an example of a nucleic acid extraction method using the magnetic bead reagent. FIG. 2 is a cross-sectional view schematically showing magnetic beads contained in the magnetic bead reagent according to the embodiment.

The nucleic acid extraction method shown in FIG. 1 includes a dispersion step S102, a mixing step S104, a separation step S106, a cleaning step S108, and an elution step S110.

1.1. Dispersion Step

In the dispersion step S102, magnetic beads 2 shown in FIG. 2 and a surfactant are dispersed in a dispersion medium. In the dispersion, for example, ultrasonic irradiation or the like is used. Accordingly, the magnetic beads 2 are substantially uniformly dispersed in the dispersion medium.

The surfactant reduces surface tension of the magnetic bead reagent and prevents aggregation of the magnetic beads 2. Accordingly, dispersibility in the dispersion medium is improved.

1.1.1. Magnetic Beads

Each of the magnetic beads 2 shown in FIG. 2 contains a Fe-based metal soft magnetic particle 21 and a silica film 22 covering the Fe-based metal soft magnetic particle 21. The Fe-based metal soft magnetic particle 21 is a particle made of a Fe-based metal and having soft magnetism. The silica film 22 is a film having a hydrophilic surface capable of adsorbing and holding the nucleic acid. The expression "adsorbing" refers to reversible physical bonding. By providing the silica film 22 having a predetermined thickness, damage to the silica film 22 is prevented even when friction occurs between the magnetic beads 2 due to the ultrasonic irradiation or the like. Accordingly, Fe-based metal soft magnetic particles 21 are less likely to be exposed, and thus elution of Fe ions and the like can be prevented.

The magnetic beads 2 have magnetization, and are thus magnetically attracted by applying an external magnetic field. Therefore, by using the magnetic beads 2, the magnetic beads 2 on which the nucleic acid is adsorbed, that is, a solid phase, can be selectively separated from a liquid phase containing impurities.

The Fe-based metal is a metal containing Fe as a main component. The main component means that a content ratio of Fe in the Fe-based metal is 50% or more in terms of atomic ratio. Such a Fe-based metal has higher saturation magnetization and higher toughness and hardness as compared with those of ferrite or the like. Thus, the Fe-based metal has excellent magnetic separability and good durability. In addition, the soft magnetism refers to a property in which coercive force is low and magnetic permeability is high.

The Fe-based metal may contain, in addition to Fe, an element that exhibits ferromagnetism alone such as Ni or Co, and may contain at least one element selected from the group consisting of Cr, Nb, Cu, Al, Mn, Mo, Si, Sn, B, C, P, Ti, and Zr according to target characteristics. In addition, the Fe-based metal may contain inevitable impurities as long as effects of the embodiment are not impaired.

The inevitable impurities are impurities that are unintentionally mixed in with a raw material or during production. Examples of the inevitable impurities include O, N, S, Na, Mg, and K.

Examples of such a Fe-based metal include, but not particularly limited to, pure iron, carbonyl iron, Fe—Si—Al based alloys such as Sendust, and Fe-based alloys such as Fe—Ni based, Fe—Co based, Fe—Ni—Co based, Fe—Si—B based, Fe—Si—B—C based, Fe—Si—B—Cr—C based, Fe—Si—Cr based, Fe—B based, Fe—P—C based, Fe—Co—Si—B based, Fe—Si—B—Nb based, Fe—Si—B—Nb—Cu based, Fe—Zr—B based, Fe—Cr based, and Fe—Cr—Al based alloys.

The Fe-based metal may be a Fe-based amorphous metal or a Fe-based crystalline metal, and the Fe-based amorphous metal is preferably used. Since the amorphous metal has higher toughness and hardness as compared with those of a metal oxide or the like, it is possible to prevent wear, loss, and accordingly elution of metal ions, in particular, the elution of the Fe ions.

The Fe-based metal soft magnetic particles 21 may be particles produced by any method. Examples of the production method include various atomization methods such as a water atomization method, a gas atomization method, and a spinning water atomization method, and a pulverization method. Among these, according to the atomization methods, the Fe-based metal soft magnetic particles 21 having a particle shape closer to a true sphere are obtained. Such Fe-based metal soft magnetic particles 21 have a high filling rate and contribute to realization of the magnetic beads 2 in which a recovery amount of the nucleic acid per unit volume is large.

A metal powder produced by the above production method may be classified by various classifiers, and the metal powder whose particle size is adjusted may be used as the Fe-based metal soft magnetic particles 21.

Saturation magnetization of the magnetic beads 2 is preferably 50 emu/g or more and 250 emu/g or less, and more preferably 100 emu/g or more and 200 emu/g or less. When the saturation magnetization of the magnetic beads 2 is within the above range, sufficient magnetic attractive force acts on the magnetic beads 2, and the magnetic beads 2 can be more reliably fixed. Accordingly, the liquid phase and the solid phase can be separated from each other more accurately.

The saturation magnetization of the magnetic beads 2 is measured using, for example, a vibrating sample magnetometer (VSM). In addition, saturation magnetization of the Fe-based metal soft magnetic particles 21 may be regarded as the saturation magnetization of the magnetic beads 2.

Coercive force of the magnetic beads 2 is preferably 100 [Oe] or less, more preferably 30 [Oe] or less, and still more preferably 10 [Oe] or less. Since such magnetic beads 2 have sufficiently low coercive force, the magnetic beads 2 are magnetized only when an external magnetic field is applied, and return to an original state when the application of the external magnetic field is stopped. Therefore, by using such magnetic beads 2, it is possible to improve operability when performing an operation of magnetic attraction by the external magnetic field and thereafter performing an operation of releasing the magnetic attraction.

The coercive force of the magnetic beads 2 is measured using, for example, a vibrating sample magnetometer (VSM). In addition, coercive force of the Fe-based metal soft magnetic particles 21 may be regarded as the coercive force of the magnetic beads 2.

An average particle size of the magnetic beads 2 is preferably 0.05 μm or more and 10.0 μm or less, more preferably 0.10 μm or more and 5.0 μm or less, and still more preferably 0.3 μm or more and 2.0 μm or less. When the average particle size of the magnetic beads 2 is within the above range, a specific surface area of the magnetic beads 2 is sufficiently large, and thus the recovery amount of the nucleic acid can be increased. When the average particle size of the magnetic beads 2 is less than the lower limit value described above, the magnetic beads 2 are likely to aggregate, adsorption efficiency for the nucleic acid may decrease, and the recovery amount of the nucleic acid may decrease. On the other hand, when the average particle size of the magnetic beads 2 exceeds the upper limit value described above, the specific surface area of the magnetic beads 2 is small, and thus the recovery amount of the nucleic acid may decrease. In addition, depending on magnitude of the magnetic attractive force, operability of an operation of fixing the magnetic beads 2 by the magnetic attraction may decrease.

The average particle size of the magnetic beads 2 is obtained as a particle size D50 at a cumulative percentage of 50% from a small diameter side in a volume-based particle size distribution obtained by a laser diffraction method.

A constituent material of the silica film 22 is not particularly limited as long as it is a material capable of forming the hydrophilic surface described above, and is, for example, a material containing silicon dioxide. Specific examples of the constituent material include silica, silicon-containing glass, and diatomaceous earth. In addition, a composite material obtained by modifying a material containing these silicon oxides may be used on a surface of any material.

An average thickness of the silica film 22 is 20 nm or more, preferably 30 nm or more, and more preferably 40 nm or more. When the average thickness of the silica film 22 is within the above range, the silica film 22 is uniformly formed, and thus it is possible to more reliably prevent the elution of the Fe ions or the like associated with the ultrasonic irradiation.

An upper limit value of the average thickness of the silica film 22 is not particularly limited, and is preferably 1000 nm or less, and more preferably 500 nm or less in consideration of a ratio of the metal in the entire magnetic beads 2, adhesion of the silica film 22, and the like.

The average thickness of the silica film 22 is a value obtained by observing cross sections of the magnetic beads 2 with an electron microscope and averaging film thicknesses at 10 or more positions. It is preferable that measurement positions extend over different magnetic beads 2.

A method of forming the silica film 22 is not particularly limited, and examples thereof include a wet film forming method such as a sol-gel method and a dry film forming method such as a vapor-phase film forming method. Among these, the sol-gel method is useful because the silica film 22 can be uniformly formed at a low cost.

A content ratio of the Fe-based metal in the magnetic beads 2 is preferably 50% by volume or more, more preferably 70% by volume or more, and still more preferably 90% by volume or more. Since such magnetic beads 2 have a sufficiently high content ratio of the Fe-based metal, it is possible to obtain large magnetic attractive force even when the magnetic beads 2 have a small diameter. On the other hand, when the content ratio of the Fe-based metal is less than the lower limit value described above, the magnetic attractive force may decrease, and separability between the magnetic beads 2 and the liquid phase may decrease.

The content ratio of Fe-based metal in the magnetic beads 2 is calculated based on an area ratio occupied by the Fe-based metal by observing the cross sections of the magnetic beads 2 with an electron microscope. If necessary, the area ratio occupied by the Fe-based metal may be calculated by element mapping.

A content ratio of the magnetic beads 2 in the magnetic bead reagent is not particularly limited, and is preferably 10% by mass or more and 70% by mass or less, more preferably 20% by mass or more and 50% by mass or less, and still more preferably 30% by mass or more and 45% by mass or less. By setting the content ratio of the magnetic beads 2 within the above range, the nucleic acid can be efficiently recovered. In addition, it is possible to prevent an increase in collision frequency between the magnetic beads 2 due to the ultrasonic irradiation or the like and to prevent wear of the silica film 22.

1.1.2. Surfactant

Examples of the surfactant include a nonionic surfactant, a cationic surfactant, an anionic surfactant, and an amphoteric surfactant, and the nonionic surfactant is preferably used. Accordingly, when the nucleic acid after extraction is analyzed, an influence of an ionic surfactant is prevented. As a result, it is possible to perform analysis by an electrophoresis method and to broaden options for analysis methods.

Examples of the nonionic surfactant include a triton-based surfactant such as Triton (registered trademark)-X and a tween-based surfactant such as Tween (registered trademark) 20, and acylsorbitan. Examples of the cationic surfactant include dodecyltrimethylammonium bromide, dodecyltrimethylammonium chloride, and cetyltrimethylammonium bromide. Examples of the anionic surfactant include sodium dodecyl sulfate (SDS), sodium N-lauroyl sarcosine, sodium cholate, sodium lauryl sulfate, and sarcosine. Examples of the amphoteric surfactant include phosphatidylethanolamine. These surfactants may be used alone or in combination of two or more thereof.

A content of the surfactant in the magnetic bead reagent is preferably equal to or larger than a critical micelle concentration of the surfactant. The critical micelle concentration is also referred to as cmc, and refers to a concentration at which molecules of a surfactant dispersed in a liquid aggregate to form a micelle. When the content of the surfactant is equal to or larger than the critical micelle concentration, the surfactant easily forms a layer around the magnetic beads 2. Accordingly, effects of preventing the aggregation of the magnetic beads 2 can be further improved.

The content of the surfactant is not limited to being equal to or larger than the critical micelle concentration, and may be less than the critical micelle concentration. For example, the content of the surfactant in the magnetic bead reagent is preferably 0.05% by mass or more and 3.0% by mass or less regardless of the critical micelle concentration.

In the ultrasonic irradiation, for example, an ultrasonic disperser such as an ultrasonic homogenizer is used. With the ultrasonic irradiation, minute bubbles (cavitation) are generated, and the magnetic beads 2 and the surfactant can be dispersed more uniformly.

On the other hand, when an impact is applied to the magnetic beads 2 due to the ultrasonic irradiation, the silica film 22 may be damaged. As reasons that the silica film 22 is damaged, collision between the magnetic beads 2, cavitation, and erosion are considered. When silica films 22 are damaged, the Fe-based metal soft magnetic particles 21 are exposed, and Fe ions and the like may be eluted.

In contrast, when the surfactant is added to the magnetic bead reagent and the average thickness of the silica film 22 is within the above range, damage to the silica film 22 due to the ultrasonic irradiation is sufficiently prevented. As a result, the elution of the Fe ions and the like is prevented. In addition, the aggregation of the magnetic beads 2 is prevented, and the magnetic beads 2 can be favorably dispersed in the magnetic bead reagent, so that the adsorption efficiency for the nucleic acid can be easily improved.

It is considered that the surfactant reduces the surface tension of the magnetic bead reagent to prevent wear of substances due to the cavitation and erosion. When the surfactant is added, the surface tension of the magnetic bead reagent decreases. It is known that there is a positive correlation between the surface tension and the wear of substances due to the cavitation and erosion. Therefore, by reducing the surface tension of the magnetic bead reagent with an action of the surfactant, damage to the silica film 22 due to the cavitation and erosion can be prevented.

A time for the ultrasonic irradiation is not particularly limited, and is preferably 1 minute or longer and 60 minutes or shorter, and more preferably 5 minutes or longer and 40 minutes or shorter.

1.1.3. Dispersion Medium

Examples of the dispersion medium include water, saline, polar organic solvents such as alcohols, and aqueous solutions of the polar organic solvents.

Examples of water include sterilized water and pure water. Examples of the alcohols include ethanol and isopropyl alcohol.

The magnetic bead reagent may contain components other than those described above.

As described above, the magnetic bead reagent according to the embodiment contains the magnetic beads 2, the surfactant, and the dispersion medium in which the magnetic beads 2 are dispersed. The magnetic beads 2 each contain the Fe-based metal soft magnetic particle 21 and the silica film 22 having an average thickness of 20 nm or more and covering the Fe-based metal soft magnetic particle 21.

According to such a configuration, the magnetic bead 2 contains the Fe-based metal soft magnetic particle 21 having higher magnetization than that of ferrite or the like and the silica film 22 having a sufficient thickness, and the magnetic bead reagent contains the surfactant. Therefore, damage to the silica film 22 due to the ultrasonic irradiation or the like can be prevented, and the elution of the Fe ions can be prevented. In addition, since the surface tension of the magnetic bead reagent is reduced by the surfactant, the magnetic beads 2 can be favorably dispersed. Accordingly, the adsorption efficiency for the nucleic acid can be improved.

1.2. Mixing Step

In the mixing step S104, a sample containing a nucleic acid is charged into a container, and the magnetic bead reagent and a Lysis and Binding Solution are mixed in the container. Accordingly, the nucleic acid is adsorbed to the magnetic beads 2.

As the Lysis and Binding Solution, for example, a liquid containing a chaotropic substance is used. The chaotropic substance has a function of generating a chaotropic ion in an aqueous solution and increasing water solubility of hydrophobic molecules, and contributes to adsorption of the nucleic acid to the magnetic beads 2. The chaotropic ion is a monovalent anion having a large ionic radius. Examples of the chaotropic substance include guanidine thiocyanate, guanidine hydrochloride, sodium iodide, potassium iodide, and sodium perchlorate. Among these, guanidine thiocyanate or guanidine hydrochloride having a strong protein denaturation effect is preferably used.

A concentration of the chaotropic substance in the Lysis and Binding Solution varies depending on the chaotropic substance, and is preferably, for example, 1.0 M or more and 8.0 M or less. In particular, when guanidine thiocyanate is used, the concentration thereof is preferably 3.0 M or more and 5.5 M or less. Further, in particular, when guanidine hydrochloride is used, the concentration thereof is preferably 4.0 M or more and 7.5 M or less.

The Lysis and Binding Solution may contain a surfactant. The surfactant is used to destroy a cell membrane or cause denaturation of a protein contained in a cell. The surfactant is not particularly limited, and examples thereof include a nonionic surfactant such as a triton-based surfactant and a tween-based surfactant, and an anionic surfactant such as sodium N-lauroyl sarcosine. Among these, the nonionic surfactant is preferable. Accordingly, when the nucleic acid after extraction is analyzed, an influence of the ionic surfactant is prevented. As a result, it is possible to perform analysis by an electrophoresis method and broaden options for analysis methods.

A concentration of the surfactant in the Lysis and Binding Solution is not particularly limited, and is preferably 0.1% by mass or more and 2.0% by mass or less.

The Lysis and Binding Solution may contain at least one of a reducing agent and a chelating agent. Examples of the reducing agent include 2-mercaptoethanol and dithiothreitol. Examples of the chelating agent include disodium salt dihydrate (EDTA).

A concentration of the reducing agent in the Lysis and Binding Solution is not particularly limited and is preferably 0.2 M or less. A concentration of the chelating agent in the Lysis and Binding Solution is not particularly limited and is preferably 0.2 mM or less.

A pH of the Lysis and Binding Solution is not particularly limited and is preferably neutral at 6 or more and 8 or less.

In the mixing step S104, if necessary, contents in the container are stirred by an ultrasonic homogenizer, a vortex mixer, shaking with a hand, or the like. A stirring time is not particularly limited and is preferably 5 seconds or longer and 30 minutes or shorter.

1.3. Separation Step

In the separation step S106, an external magnetic field is caused to act on the magnetic beads 2 on which the nucleic acid is adsorbed, and the magnetic beads 2 are magnetically attracted. Accordingly, the magnetic beads 2 are moved to and fixed to a wall surface of the container. As a result, the magnetic beads 2 in the solid phase can be separated from the liquid phase.

In the separation step S106, in a state in which an external magnetic field is applied, if necessary, the contents in the container are stirred by an ultrasonic homogenizer, a vortex mixer, shaking with a hand, or the like. This increases a probability that the magnetic beads 2 are magnetically attracted to the external magnetic field.

After the magnetic beads 2 are fixed, acceleration may be applied to the container as necessary. Accordingly, a liquid attached to the magnetic beads 2 can be shaken off, so that the solid phase and the liquid phase can be separated from each other more accurately. The acceleration may be centrifugal acceleration. To apply the centrifugal acceleration, a centrifugal separator may be used.

After the magnetic beads 2 and the liquid phase are separated from each other as described above, the liquid phase in the container is discharged by a pipette or the like in a state in which the magnetic beads 2 are fixed to the wall surface of the container.

1.4. Cleaning Step

In the cleaning step S108, the magnetic beads 2 on which the nucleic acid is adsorbed are cleaned. The cleaning is an operation of removing impurities by bringing the magnetic beads 2 on which the nucleic acid is adsorbed into contact with a cleaning liquid and then separating the magnetic beads 2 from the cleaning liquid again in order to remove the impurities adsorbed on the magnetic beads 2.

Specifically, first, the cleaning liquid is supplied into the container by a pipette or the like. Then, the magnetic beads 2 and the cleaning liquid are stirred. Accordingly, the cleaning liquid is brought into contact with the magnetic beads 2, and the magnetic beads 2 on which the nucleic acid is adsorbed are cleaned. At this time, the external magnetic field may be temporarily removed. Accordingly, the magnetic beads 2 are dispersed in the cleaning liquid, so that cleaning efficiency can be further improved.

Next, the magnetic beads 2 are fixed again, and the cleaning liquid is discharged. By repeating supply and discharge of the cleaning liquid as described above once or more, the magnetic beads 2 can be cleaned.

The cleaning liquid is not particularly limited as long as it is a liquid that does not promote elution of the nucleic acid and does not promote binding of impurities to the magnetic beads 2. Examples thereof include organic solvents such as ethanol, isopropyl alcohol, and acetone, aqueous solutions of the organic solvents, and a low salt concentration aqueous solution. Examples of the low salt concentration aqueous solution include a buffer solution. A salt concentration in the low salt concentration aqueous solution is preferably 0.1 mM or more and 100 mM or less, and more preferably 1 mM or more and 50 mM or less. A salt in the buffer solution is not particularly limited, and a salt such as Tris, Hepes, Pipes, and phosphoric acid is preferably used.

The cleaning liquid may contain a surfactant such as Triton (registered trademark), Tween (registered trademark), or SDS. A pH of the cleaning liquid is not particularly limited.

In the cleaning step S108, in a state in which the cleaning liquid is brought into contact with the magnetic beads 2, if necessary, the contents in the container are stirred by an ultrasonic homogenizer, a vortex mixer, shaking with a hand, or the like. Accordingly, the cleaning efficiency can be improved.

The cleaning step S108 may be performed as necessary and may be omitted when cleaning is not necessary.

1.5. Elution Step

In the elution step S110, the nucleic acid is eluted from the magnetic beads 2 on which the nucleic acid is adsorbed. The elution is an operation of transferring the nucleic acid to an eluate by bringing the magnetic beads 2 on which the nucleic acid is adsorbed into contact with the eluate and then separating the magnetic beads 2 from the eluate again.

Specifically, first, the eluate is supplied into the container by a pipette or the like. Then, the magnetic beads 2 and the eluate are stirred. Accordingly, the eluate is brought into contact with the magnetic beads 2, and the nucleic acid can be eluted. At this time, the external magnetic field may be temporarily removed. Accordingly, the magnetic beads 2 are dispersed in the eluate, so that elution efficiency can be further improved.

Next, the magnetic beads 2 are fixed again, and the eluate from which the nucleic acid is eluted is discharged. Accordingly, the nucleic acid can be recovered.

The eluate is not particularly limited as long as it is a liquid that promotes the elution of the nucleic acid from the magnetic beads 2 on which the nucleic acid is adsorbed. For example, in addition to water such as sterilized water or pure water, a TE buffer solution, that is, an aqueous solution containing 10 mM Tris-HCl buffer solution and 1 mM EDTA and having a pH of 8 is preferably used.

The eluate may contain a surfactant such as Triton (registered trademark), Tween (registered trademark), or SDS.

In the elution step S110, in a state in which the eluate is brought into contact with the magnetic beads 2 on which the nucleic acid is adsorbed, if necessary, the contents in the container are stirred by an ultrasonic homogenizer, a vortex mixer, shaking with a hand, or the like. Accordingly, the elution efficiency can be improved.

In the elution step S110, the eluate may be heated. Accordingly, the elution of the nucleic acid can be promoted. A heating temperature for the eluate is not particularly limited, and is preferably 70° C. or higher and 200° C. or lower, more preferably 80° C. or higher and 150° C. or lower, and still more preferably 95° C. or higher and 125° C. or lower.

Examples of a heating method include a method in which an eluate heated in advance is supplied, and a method in which an unheated eluate is supplied into a container and then heated. A heating time is not particularly limited and is preferably 30 seconds or longer and 10 minutes or shorter.

The elution step S110 may be performed as necessary, and for example, when only the separation of the magnetic beads 2 from the liquid phase in the separation step S106 is the purpose, the elution step S110 may be omitted.

The magnetic bead reagent according to the present disclosure is described above based on the illustrated embodiment, but the present disclosure is not limited thereto. For example, in the magnetic bead reagent according to the present disclosure, each part of the above embodiment may be replaced with any configuration having the same function, and any constituent may be added to the above embodiment.

EXAMPLES

Next, specific examples of the present disclosure will be described.

2. Recovery of Nucleic Acid

2.1. Example 1

First, a magnetic bead reagent charged in a container was irradiated with ultrasonic waves for 30 minutes to disperse magnetic beads. A mass of the magnetic beads used was 23 mg.

Next, the magnetic bead reagent, *E. coli* DNA (sample), and a Lysis and Binding Solution were mixed. Then, contents in the container were stirred for 10 minutes by a vortex mixer. A content ratio of the *E. coli* DNA with respect to a volume of the contents in the container was 20 ng/μL.

Next, in a state in which the magnetic beads were magnetically separated, a liquid phase was discharged, and a cleaning liquid was supplied instead. Then, the contents in the container were stirred and the magnetic beads were cleaned. As the cleaning liquid, an aqueous guanidine hydrochloride solution having a concentration of 8 M and an aqueous ethanol solution having a concentration of 70% were used. Then, cleaning using the former cleaning liquid was performed twice, and then cleaning using the latter cleaning liquid was performed twice.

Next, in a state in which the magnetic beads were magnetically separated, the liquid phase was discharged, and an eluate was supplied instead. Then, the contents in the container were stirred to elute the nucleic acid. Pure water was used as the eluate.

Next, in a state in which the magnetic beads were magnetically separated, the eluate was discharged and recovered. Accordingly, the nucleic acid in the sample was recovered.

2.2. Examples 2 to 8

A nucleic acid in a sample was recovered in the same manner as in Example 1 except that configurations of magnetic bead reagents were changed as shown in Table 1.

2.3. Comparative Example 1

A nucleic acid in a sample was recovered in the same manner as in Example 1 except that addition of a surfactant was omitted.

2.4. Comparative Example 2

A nucleic acid in a sample was recovered in the same manner as in Example 2 except that an average thickness of a silica film was 10 nm.

2.5. Comparative Example 3

A nucleic acid in a sample was recovered in the same manner as in Example 3 except that addition of a surfactant was omitted.

3. Evaluation of Recovered Nucleic Acid

3.1. Concentration of Recovered Nucleic Acid

For each of the nucleic acids recovered using the magnetic bead reagents according to Examples and Comparative Examples, a recovery amount was measured by a real-time PCR apparatus manufactured by Thermo Fisher Scientific Inc., and a concentration of the nucleic acid in the eluate was calculated. Then, the calculated concentration was evaluated in light of the following evaluation criteria.

AA: the concentration of the recovered nucleic acid is 12 ng/μL or more

A: the concentration of the recovered nucleic acid is 8 ng/μL or more and less than 12 ng/μL B: the concentration of the recovered nucleic acid is 4 ng/μL or more and less than 8 ng/μL C: the concentration of the recovered nucleic acid is less than 4 ng/μL Evaluation results are shown in Table 1.

3.2. Analyzability by Electrophoresis Method

For each of the nucleic acids recovered using the magnetic bead reagents according to Examples and Comparative Examples, analyzability by an electrophoresis method was evaluated in light of the following evaluation criteria.

Yes: the analysis by an electrophoresis method is possible

No: the analysis by an electrophoresis method is impossible

Evaluation results are shown in Table 1.

TABLE 1

| | | | | | Example 1 mass % | Example 2 mass % | Example 3 mass % | Example 4 mass % |
|---|---|---|---|---|---|---|---|---|
| Configuration of magnetic bead reagent | Magnetic beads 1 | Average particle size | 3.0 | μm | 38 | 38 | — | 38 |
| | | Average thickness of silica film | 40 | nm | | | | |
| | Magnetic beads 2 | Average particle size | 3.0 | μm | — | — | — | — |
| | | Average thickness of silica film | 10 | nm | | | | |
| | Magnetic beads 3 | Average particle size | 0.8 | μm | — | — | 38 | — |
| | | Average thickness of silica film | 40 | nm | | | | |
| | Magnetic beads 4 | Average particle size | 5.0 | μm | — | — | — | — |
| | | Average thickness of silica film | 20 | nm | | | | |
| | Magnetic beads 5 | Average particle size | 1.5 | μm | — | — | — | — |
| | | Average thickness of silica film | 30 | nm | | | | |
| | Surfactant | Nonionic (Triton-X100) cmc: 0.1% | | | 0.05 | 0.10 | 0.10 | — |
| | | Anionic (SDS) cmc: 0.1% | | | — | — | — | 0.10 |
| | Pure water | — | | | Remainder | Remainder | Remainder | Remainder |
| Evaluation result of recovered nucleic acid | Concentration of recovered nucleic acid | | | | B | A | AA | B |
| | Analyzability by electrophoresis method | | | | Yes | Yes | Yes | No |

| | | | | | Example 5 mass % | Example 6 mass % | Example 7 mass % | Example 8 mass % |
|---|---|---|---|---|---|---|---|---|
| Configuration of magnetic bead reagent | Magnetic beads 1 | Average particle size | 3.0 | μm | — | — | 30 | 45 |
| | | Average thickness of silica film | 40 | nm | | | | |
| | Magnetic beads 2 | Average particle size | 3.0 | μm | — | — | — | — |
| | | Average thickness of silica film | 10 | nm | | | | |
| | Magnetic beads 3 | Average particle size | 0.8 | μm | — | — | — | — |
| | | Average thickness of silica film | 40 | nm | | | | |

TABLE 1-continued

| | | | | | | | | |
|---|---|---|---|---|---|---|---|---|
| | Magnetic beads 4 | Average particle size | 5.0 | µm | 38 | — | — | — |
| | | Average thickness of silica film | 20 | nm | | | | |
| | Magnetic beads 5 | Average particle size | 1.5 | µm | — | 38 | — | — |
| | | Average thickness of silica film | 30 | nm | | | | |
| | Surfactant | Nonionic (Triton-X100) cmc: 0.1% | | | 0.15 | 0.10 | 0.10 | 0.10 |
| | | Anionic (SDS) cmc: 0.1% | | | — | — | — | — |
| | Pure water | — | | | Remainder | Remainder | Remainder | Remainder |
| Evaluation result of recovered nucleic acid | Concentration of recovered nucleic acid | | | | B | AA | A | A |
| | Analyzability by electrophoresis method | | | | Yes | Yes | Yes | Yes |

| | | | | | Comparative Example 1 mass % | Comparative Example 2 mass % | Comparative Example 3 mass % |
|---|---|---|---|---|---|---|---|
| Configuration of magnetic bead reagent | Magnetic beads 1 | Average particle size | 3.0 | µm | 38 | — | — |
| | | Average thickness of silica film | 40 | nm | | | |
| | Magnetic beads 2 | Average particle size | 3.0 | µm | — | 38 | — |
| | | Average thickness of silica film | 10 | nm | | | |
| | Magnetic beads 3 | Average particle size | 0.8 | µm | — | — | 38 |
| | | Average thickness of silica film | 40 | nm | | | |
| | Magnetic beads 4 | Average particle size | 5.0 | µm | — | — | — |
| | | Average thickness of silica film | 20 | nm | | | |
| | Magnetic beads 5 | Average particle size | 1.5 | µm | — | — | — |
| | | Average thickness of silica film | 30 | nm | | | |
| | Surfactant | Nonionic (Triton-X100) cmc: 0.1% | | | — | 0.10 | — |
| | | Anionic (SDS) cmc: 0.1% | | | — | — | — |
| | Pure water | — | | | Remainder | Remainder | Remainder |
| Evaluation result of recovered nucleic acid | Concentration of recovered nucleic acid | | | | C | C | C |
| | Analyzability by electrophoresis method | | | | No | No | No |

As shown in Table 1, it is recognized that the nucleic acid can be recovered at a high concentration by using the magnetic bead reagents in Examples. In particular, it is recognized that the analysis by the electrophoresis method is possible when the magnetic bead reagent contains a nonionic surfactant. In magnetic bead reagents in Examples, an increase in Fe ions is not observed even after ultrasonic irradiation.

In contrast, magnetic bead reagents in Comparative Examples 1 and 3 do not contain a surfactant, and thus the concentration of the nucleic acid recovered using the magnetic bead reagent is low. In addition, for the magnetic bead reagent in Comparative Example 2, the average thickness of the silica films in the magnetic beads is small, and the concentration of the nucleic acid recovered using the magnetic bead reagent is low.

In the magnetic bead reagents in Comparative Examples, an increase in Fe ions is observed after the ultrasonic irradiation. Therefore, it is considered that a low concentration of the recovered nucleic acid is influenced by eluted Fe ions. The nucleic acids recovered using the magnetic bead reagents in Comparative Examples cannot be analyzed by the electrophoresis method due to an influence of elution of the Fe ions.

What is claimed is:

1. A magnetic bead reagent comprising:

a magnetic bead containing a Fe-based metal soft magnetic particle and a silica film that has an average thickness of 20 nm or more and that covers the Fe-based metal soft magnetic particle;

a surfactant; and a dispersion medium in which the magnetic bead is dispersed, wherein an average particle size of the magnetic bead is 1.5 μm or more and 10.0 μm or less, and wherein a content ratio of the magnetic beads in the magnetic bead reagent is 30% by mass or more and 45% by mass or less.

2. The magnetic bead reagent according to claim 1, wherein the surfactant is a nonionic surfactant.

3. The magnetic bead reagent according to claim 1, wherein a content of the surfactant is equal to or larger than a critical micelle concentration of the surfactant.

4. The magnetic bead reagent according to claim 1, wherein saturation magnetization of the magnetic bead is 50 emu/g or more and 250 emu/g or less.

5. The magnetic bead reagent according to claim 1, wherein the Fe-based metal soft magnetic particle contains a Fe-based amorphous metal.

* * * * *